(12) United States Patent
Stenberg

(10) Patent No.: US 8,796,502 B2
(45) Date of Patent: Aug. 5, 2014

(54) METHOD OF MARKING AN ABSORBENT ARTICLE

(75) Inventor: Anders Stenberg, Onsala (SE)

(73) Assignee: SCA Hygiene Products AB, Gothenburg (SE)

( * ) Notice: Subject to any disclaimer, the term of this patent is extended or adjusted under 35 U.S.C. 154(b) by 782 days.

(21) Appl. No.: 11/839,589

(22) Filed: Aug. 16, 2007

(65) Prior Publication Data

US 2007/0276348 A1    Nov. 29, 2007

Related U.S. Application Data

(63) Continuation of application No. 09/879,151, filed on Jun. 13, 2001.

(60) Provisional application No. 60/211,188, filed on Jun. 13, 2000.

(30) Foreign Application Priority Data

Jun. 13, 2000  (SE) ........................... 0002206

(51) Int. Cl.
    *A61F 13/15*    (2006.01)
(52) U.S. Cl.
    USPC .......................................... 604/361
(58) Field of Classification Search
    USPC .......................................... 604/361
    See application file for complete search history.

(56) References Cited

U.S. PATENT DOCUMENTS

| 3,952,746 A | 4/1976 | Summers |
| 4,022,211 A | 5/1977 | Timmons et al. |
| 4,192,311 A * | 3/1980 | Felfoldi ................ 604/361 |
| 4,231,370 A | 11/1980 | Mroz et al. |
| 4,662,875 A | 5/1987 | Hirotsu et al. |
| 4,738,674 A | 4/1988 | Todd et al. |
| 5,354,289 A * | 10/1994 | Mitchell et al. ........... 604/361 |
| H1376 H * | 11/1994 | Osborn et al. ............. 604/361 |

(Continued)

FOREIGN PATENT DOCUMENTS

| CA | 2256049 | 6/1999 |
| EP | 0203715 | 12/1986 |

(Continued)

OTHER PUBLICATIONS

Opposition filed in a corresponding EP applicaiton.

(Continued)

*Primary Examiner* — Lynne Anderson
(74) *Attorney, Agent, or Firm* — Buchanan Ingersoll & Rooney PC

(57) ABSTRACT

A method of marking an absorbent article which has a liquid pervious top sheet, a liquid impervious back sheet, and an absorbent body enclosed there between. The method includes providing at least one strip on an inside of the back sheet material, i.e., on the side adjacent the absorbent body, wherein a color or tint of the strip is different from the rest of the back sheet material and wherein the color or tint of the strip is selected so as to be an indication of product type, product size, or product absorption capacity of the absorbent article; and arranging a wetness indicator on or adjacent the at least one strip on the inside of the liquid impervious back sheet so that the wetness indicator is visible through the back sheet material.

25 Claims, 3 Drawing Sheets

(56) References Cited

U.S. PATENT DOCUMENTS

| | | | |
|---|---|---|---|
| 5,531,731 A * | 7/1996 | Brusky | 604/390 |
| 5,766,212 A * | 6/1998 | Jitoe et al. | 604/361 |
| 5,839,585 A | 11/1998 | Miller | |
| 5,902,296 A | 5/1999 | Fluyeras | |
| 5,947,943 A | 9/1999 | Lee | |
| 6,030,373 A | 2/2000 | Van Gompel et al. | |
| 6,059,710 A | 5/2000 | Rajala et al. | |
| 6,307,119 B1 | 10/2001 | Cammarota et al. | |
| 6,747,185 B2 * | 6/2004 | Inoue et al. | 604/361 |

FOREIGN PATENT DOCUMENTS

| | | |
|---|---|---|
| EP | 0211524 | 2/1987 |
| EP | 0496567 A2 | 7/1992 |
| EP | 0925769 | 6/1999 |
| EP | 0951889 A1 | 10/1999 |
| FR | 2711317 | 8/1998 |
| GB | 2327354 | 1/1999 |
| JP | S59-024704 | 2/1984 |
| JP | H10-075980 | 3/1998 |
| RU | 2145830 | 2/2000 |
| WO | 9500099 | 1/1995 |
| WO | 9916401 | 4/1999 |

OTHER PUBLICATIONS

Translation of Colombian Office Action issued in a corresponding application.

* cited by examiner

METHOD OF MARKING AN ABSORBENT ARTICLE

CROSS-REFERENCE TO RELATED APPLICATIONS

The present application is a continuation of U.S. Ser. No. 09/879,151, which was filed on Jun. 13, 2001, and which claims the benefit of U.S. Provisional Application No. 60/211,188, filed on Jun. 13, 2000, and which claims priority of SE 0002206-1, filed in Sweden on Jun. 13, 2000, and the entire contents of U.S. Ser. No. 09/879,151, U.S. Provisional Application No. 60/211,188, and SE 0002206-1 are incorporated herein by reference.

TECHNICAL FIELD

The present invention refers to a method of identifying an absorbent article such as a diaper or incontinence guard comprising a liquid pervious top sheet, a liquid impervious back sheet and an absorbent body enclosed there between, at which on the inside of the liquid impervious back sheet, i.e., on the side adjacent the absorbent body, there is arranged a wetness indicator in a certain pattern, which is visible through the back sheet material.

BACKGROUND

Wetness indicators especially on diapers and incontinence guards for adult incontinent persons, have been known for several years and facilitates for the nursing staff to determine whether the diaper or incontinence guard needs to be changed. It for example known through EP-A-0 211 524 to print a pattern of a water soluble dye on the inside of the back sheet material of a diaper by means of ink beam technique. The dyestuff can alternatively be of a type that changes color or tint when brought into contact with urine. The printed pattern can also consist of symbols or codes for quality- or other manufacturing control.

It is further known through EP-A-0 203 715 to treat an absorbent body of a diaper so that it gets a tight paper like structure on the backside, which then is used as a reception surface for a wetness indicating dye applied in a pattern that is visible through the backside material of the diaper.

It is also known to have capillary wetness indicators, i.e., a thin strip or thread having a high capillary effect arranged in connection to the absorption body and which is in contact with an indicator which dissolves, changes color or tint when brought in contact with a liquid. Such wetness indicators are known through for example U.S. Pat. No. 4,738,674 and GB-A-2 327 354.

The wetness indicator can be arranged at different locations, such as along the side of the absorption body or on the underside thereof. It can be therefore be difficult for the nurse to locate the wetness indicator on the article in order to read it to see whether the article needs to be changed or not.

WO 99/16401 discloses an diaper having a wetness indicator on the inside of the back sheet material. The back sheet material is a laminate of a fibrous nonwoven material and a polymer sheet. A plurality of translucent windows are arranged in said back sheet through which the wetness indicator is visible.

U.S. Pat. No. 4,231,370 discloses a diaper having a wetness indicator in the form of a coating applied in a pattern on the inside of a translucent back sheet material.

FR-A-2 711 317 discloses a wetness indicator comprising an inner portion which changes color when it is wetted by urine and an outer portion which is translucent plastic material.

EP-A-0 925 769 discloses a diaper having a back sheet with transparent zones through which a wetness of the absorbent core can be observed.

OBJECT AND SUMMARY

An object of the present invention is to make it easier for the nurse to identify the location of the wetness indicator on the article and by that facilitate the reading thereof. This has been solved by applying the wetness indicator on or adjacent at least one strip having a color or tint different from the rest of the back sheet material. According to a preferred embodiment of the invention, the color or tint of the strip is an indication of the type, size, absorption capacity or the like of the article.

According to one embodiment, the strip is separate from the back sheet material and is applied to the inside thereof.

According to another embodiment, the strip is a part of the back sheet material which is colored in another color or tint than the rest of the back sheet material.

According to an embodiment, the strip extends in the longitudinal direction of the article over the entire or at least over a substantial part thereof.

According to another embodiment, the strip extends in the transverse direction of the article and is applied opposite the part of the article that is intended to form a fold in the folded packaging position of the article.

The width of the strip should be between 1 and 8 cm, preferably between 2 and 7 cm and more preferably between 3 and 6 cm.

On the strip or adjacent thereto there can further be printed symbols, codes or the like indication the type of product, size, absorption capacity or the like.

DESCRIPTION OF THE DRAWINGS

The invention will in the following be closer described with reference to some embodiments shown in the accompanying drawings.

DESCRIPTION OF PREFERRED EMBODIMENTS

Figure 1:
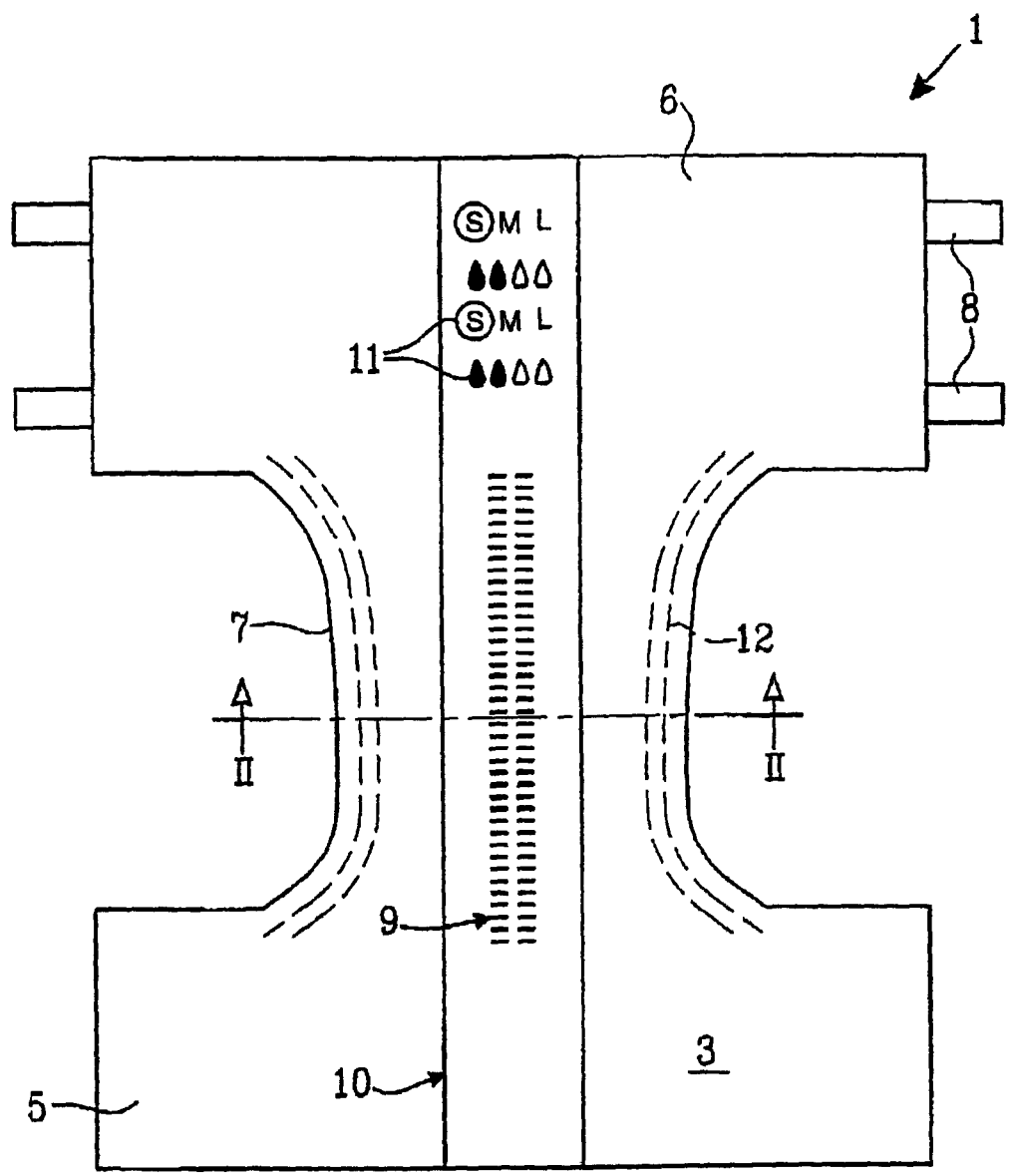
FIG. 1 is a plan view of a first embodiment of a diaper seen from the underside.
Figure 2:
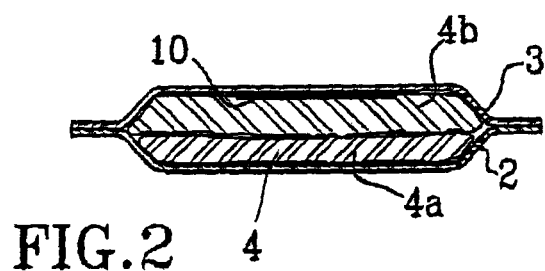
FIG. 2 is a section according to the line II-II in FIG. 1.

In FIGS. 1 and 2 there is disclosed an embodiment of a diaper 1, comprising a liquid pervious top sheet 2, a liquid impervious back sheet 3 and an absorbent body 4 enclosed there between. The absorbent body 4 can comprise two or more layers, such as liquid acquisition layer 4a and storage layer 4b.

The liquid pervious top sheet 2 can be a nonwoven material, for example a spunbond material of synthetic filaments, a meltblown material, a thermobonded material or a bonded carded fibrous web.

The liquid impervious back sheet material 3 can consist of a plastic film, a nonwoven material coated with a liquid impervious material or a hydrophobic nonwoven material which resists liquid penetration. The back sheet material can be a so called breathable material, which allows penetration of water vapour but prevents passage of liquid penetration. It may in this case be a porous plastic film, a nonwoven material or a laminate of a porous plastic film and a nonwoven material.

The top sheet 2 and the back sheet 3 have a somewhat larger extension in the plane than the absorbent body 4 and extend outside the edges thereof. The layers 2 and 3 are connected within their projecting portions, for example by gluing or welding with ultra sonic or heat.

The absorbent body 4 can be of any conventional kind. Examples of commonly occurring absorption materials are cellulosic fluff pulp, tissue layers, highly absorbent polymers (so called superabsorbents), absorbent foam materials, absorbent nonwoven materials and the like. It is common to combine cellulosic fluff pulp with superabsorbents in an absorbent body. It is also common to have absorbent bodies comprising layers of different materials with different properties with respect to liquid acquisition capacity, distribution capacity and storage capacity. This is well-known to the person skilled in the art and need therefor not be described in detail. The thin absorbent bodies that are common in for example baby diapers and incontinence guards often comprise a liquid storage layer 4b in the form of a compressed mixed or layered structure of cellulosic fluff pulp and superabsorbent and a liquid acquisition layer 4a arranged on top of the liquid storage layer, said liquid acquisition layer having an open porous structure with the ability to quickly acquire the discharged body fluid and temporarily store it before it is absorbed by the underlying storage layer 4b.

The diaper/incontinence guard is intended to enclose the lower part of the wearer's torso as a pair of absorbent pants. It is provided with a front portion 5 intended during use to be turned forwards on the user, and a rear portion 6 intended during use to be turned backwards on the user, and a narrower crotch portion 7 located between the front and rear portion, said crotch portion is intended to be applied in the crotch of the wearer between the legs. The rear portion 6 is provided with a pair of tape flaps 8 or other type of fastening means such as hook and loop type, and which are intended to be used for fasten together the diaper to the desired pantlike shape. Alternatively the fastening means can be arranged at the front portion. Around the leg portions there are arranged elastic threads 12 or the like, which provide a sealing effect around the thighs of the wearer.

Figure 4:
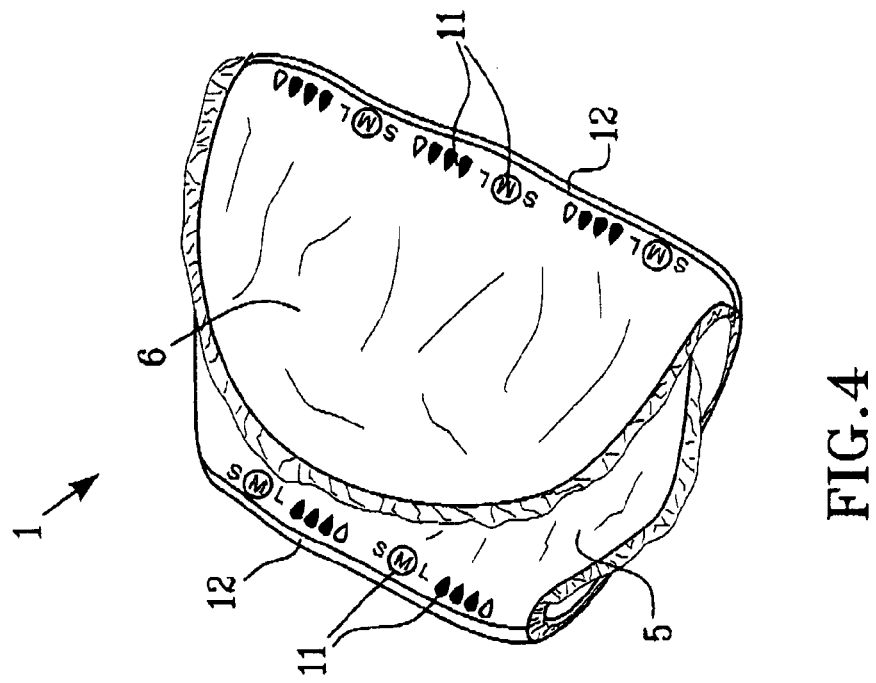
FIG. 4 shows in perspective a diaper in folded condition.
Figure 3:
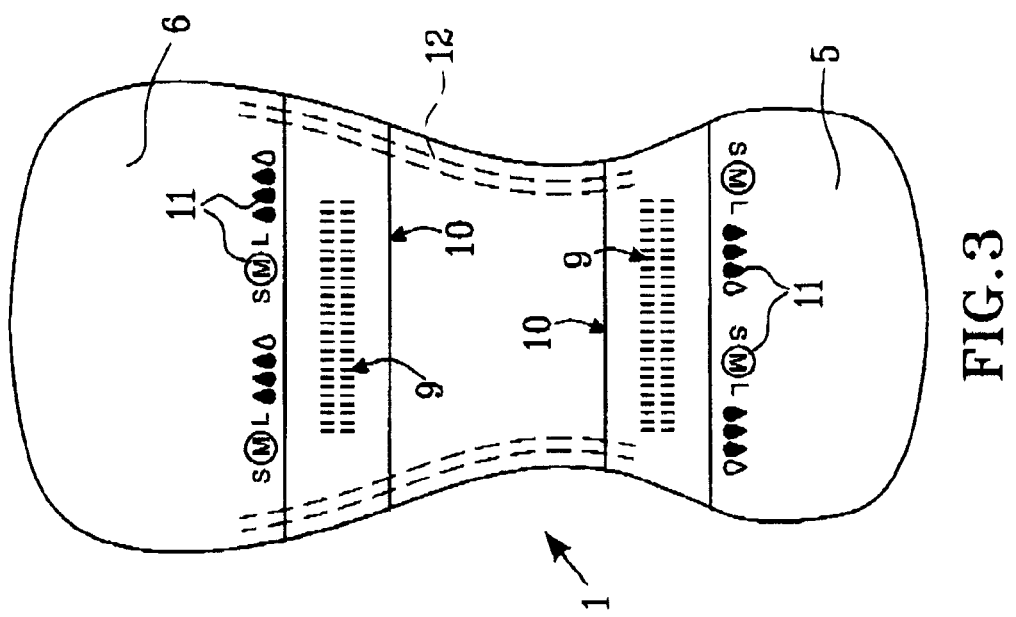
FIG. 3 is a plan view of another embodiment of an incontinence guard seen from the back side.
Figure 5:
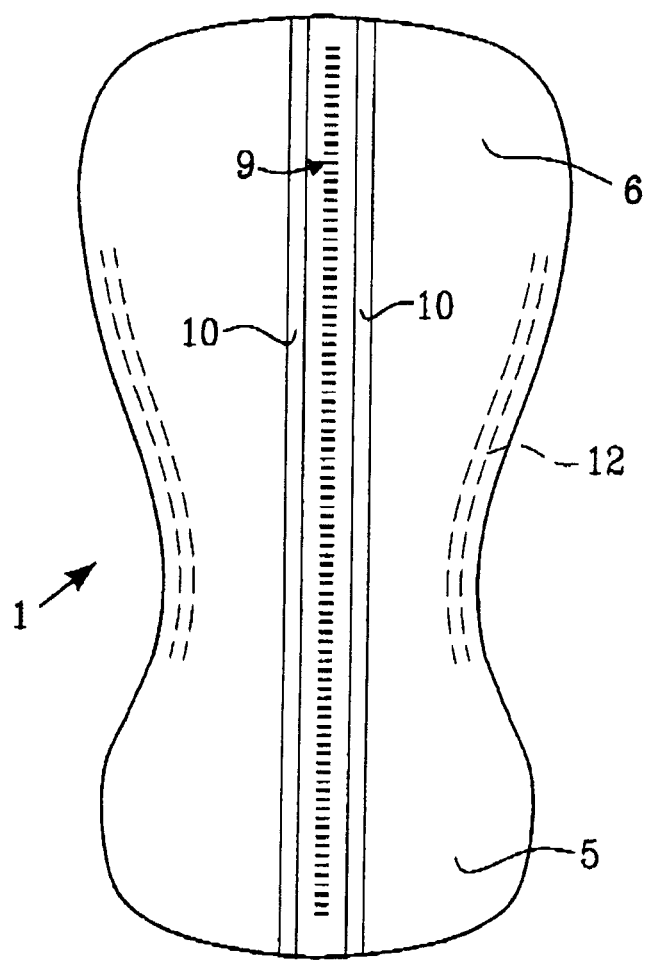
FIG. 5 is a plan view of a further embodiment of an incontinence guard seen from the backside.

In FIGS. 3-5 there are shown examples of an incontinence guard intended to be kept in place by a pair of tight pants. The fastening means in the form of tapes or hooks and loops are therefore lacking. Possibly there can on the underside of the back sheet material be applied glue strings or another kind of friction increasing means in order to keep the incontinence guard in place in the pants.

It is pointed out that the incontinence guard and the diaper shown in the drawings and described above only represent a couple of examples of absorbent articles and are by no means limiting for the present invention. Thus the shape of the article as well as its overall design can be varied. The absorbent article can also be a pant diaper, a belt-provided diaper or the like.

On the inside of the back sheet material 3 there is applied a wetness indicator 9, which preferably consists of a dyestuff which dissolves or changes color or tint when brought into contact with liquid, and which is printed directly on the back sheet material or alternatively on a separate strip that is fastened to the inside of the back-sheet material.

The wetness indicator 9 is applied on or adjacent at least one strip 10 with a color or tint that is different the rest of the back sheet material. The strip 10 either consists of a part that is separate from the back sheet material 3 and is fastened to the inside thereof, or consists of a part of the back sheet material that is colored in another color or tint than the rest of the back sheet material. The strip 10 can consist of one single colored strip or of a striped pattern or other optional pattern. The strip 10 may either be a continuous strip or may consist of several discontinuous portions arranged so as to form a discontinuous line. The strip 10 may also comprise two or more strips arranged close to each other.

In the embodiments shown in FIGS. 1-4 the wetness indicator 9 is applied on the strip 10, while in the embodiment shown in FIG. 5 it is applied between two strips 10 extending substantially in parallel.

According to a further embodiment the wetness indicator 9 may be visible through apertures or windows arranged in the strip 10.

By the fact that the wetness indicator 9 is applied on or adjacent such a strip 10, which has an appearance different from the rest of the back sheet material 3, the identification of the location of the wetness indicator 9 is facilitated. Moreover the color, tint or other appearance of the strip 10, may be an indicator of the product type, size, absorption capacity or the like. On or adjacent the strip 10 there can be further arranged symbols 11, codes or the like, which indicate the product type, size, absorption capacity or the like. By this it is easier for the nurse to find the correct type of product in the case where the articles have been taken out of their packages and placed on a shelf or the like in a storage space in a nursing home or the like.

Besides the strip 10 may also serve as an indicator of the longitudinal center of the article so that it is easier to put on the article correctly. It may also act as a longitudinal center indicator during the manufacturing process.

The strip 10 can extend in the longitudinal direction of the article, preferably centrally along the product, as is shown in FIG. 1. It is also possible that the strip 10 extends in the transverse direction of the article, as is shown in FIGS. 3 and 4. In this case the strip 10 should be arranged at the part of the product intended to form a folding line 11 in th folded package condition of the article (see FIG. 4). In the case where the article is folded along two folding line there should be strips 10 at each folding line 11, so that independently of how the article is put on the shelf on strip 10 should be visible outwards.

The width of the strip 10 should be between 1 and 8 cm, preferably between 2 and 7 cm and more preferably between 3 and 6 cm.

The invention is of course not limited to the described and illustrated embodiments but a plurality of modifications are possible within the scope of the claims, and equivalents thereof.

The invention claimed is:

1. A method of marking an absorbent article, the absorbent article comprising a liquid pervious top sheet, a liquid impervious back sheet, and an absorbent body enclosed there between, the method comprising:
providing at least one strip on the back sheet, the strip having a width of between 1 and 6 cm, wherein a color or tint of the strip is different from the rest of the back sheet and wherein the color or tint of the strip is selected so as to be an indication of product size or product absorption capacity of the absorbent article; and
arranging a wetness indicator on or adjacent the at least one strip on the inside of the liquid impervious back sheet so that the wetness indicator is visible through the back sheet and wherein the color or tint of the strip that is an indication of product size or product absorption capacity facilitates identification of the location of the wetness indicator.

2. The method of claim 1, wherein the strip is separate from the back sheet and is fastened on the inside thereof.

3. The method of claim 1, wherein the strip is a part of the back sheet.

4. The method of claim 1, wherein the strip extends in a longitudinal direction of the article over an entire or at least an essential part of the length of the article.

5. The method of claim 1, wherein the strip has a longitudinal direction and the longitudinal direction of the strip extends in a transverse direction of the article and is applied at a part of the article that forms a folding line in a folded packaging position of the article.

6. The method of claim 1, wherein the width of the strip is between 2 and 6 cm.

7. The method of claim 1, wherein the width of the strip is between 3 and 6 cm.

8. The method of claim 1, wherein on or adjacent the strip there is further printed symbols or codes which indicate the product type, size, or absorption capacity of the article.

9. The method of claim 1, wherein the color or tint of the strip is selected so as to be an indication of the size of the absorbent article.

10. The method of claim 1, wherein the color or tint of the strip is selected so as to be an indication of the absorption capacity of the absorbent article.

11. The method of claim 1, wherein the at least one strip is provided on an inside of the back sheet material or on the side adjacent the absorbent body.

12. The method of claim 1, wherein the article is an adult incontinence article.

13. The method of claim 1, wherein the strip is a single color.

14. The method of claim 1, wherein the strip is a striped pattern.

15. A method comprising:
providing an absorbent article comprising a liquid pervious top sheet, a liquid impervious back sheet, an absorbent body enclosed there between, the liquid-impervious back sheet comprising a strip part and a remaining part, the strip part being an integral part of the back sheet, the strip part having a different color than the remaining part of the back sheet, and a wetness indicator arranged at an inside of the liquid impervious back sheet in a pattern and being visible through the back sheet, wherein the wetness indicator is disposed on or adjacent to the strip part,
identifying the location of the wetness indicator on or adjacent to the strip part, wherein the identification of the location of the wetness indicator is facilitated by the strip part having a different color than the remaining part of the back sheet,
identifying the size or absorption capacity of the article by the color of the strip that is used to facilitate the identification of the location of the wetness indicator, wherein the identification of the size or absorption capacity of the article is facilitated by the color of the strip part that is used to facilitate the identification of the location of the wetness indicator also being an indicia of size or absorption capacity of the article.

16. The method of claim 15, wherein the strip is separate from the back sheet and is fastened on the inside thereof.

17. The method of claim 15, wherein the strip is a part of the back sheet.

18. The method of claim 15, wherein the strip extends in a longitudinal direction of the article over an entire or at least an essential part of the length of the article.

19. The method of claim 15, wherein the strip has a longitudinal direction and the longitudinal direction of the strip extends in a transverse direction of the article and is applied at a part of the article that forms a folding line in a folded packaging position of the article.

20. The method of claim 15, wherein the width of the strip is between 1 and 8 cm.

21. The method of claim 15, wherein the width of the strip is between 3 and 6 cm.

22. The method of claim 15, wherein the color or tint of the strip is selected so as to be an indication of the size of the absorbent article.

23. The method of claim 15, wherein the color or tint of the strip is selected so as to be an indication of the absorption capacity of the absorbent article.

24. The method of claim 15, wherein the strip is a single color.

25. The method of claim 15, wherein the strip is a striped pattern.

* * * * *